United States Patent
Kircher et al.

(10) Patent No.: US 9,892,433 B2
(45) Date of Patent: Feb. 13, 2018

(54) METHODS AND SYSTEMS FOR FACILITATING DONATION OF PRESCRIPTION MEDICATION

(71) Applicant: Supporting Initiatives to Redistribute Unused Medicine (SIRUM), Stanford, CA (US)

(72) Inventors: Adam S. Kircher, Tallahassee, FL (US); George J. Wang, Menlo Park, CA (US); Kiah J. Williams, Mountain View, CA (US)

(73) Assignee: SIRUM, Palo Alto, CA (US)

( * ) Notice: Subject to any disclaimer, the term of this patent is extended or adjusted under 35 U.S.C. 154(b) by 194 days.

(21) Appl. No.: 14/172,792

(22) Filed: Feb. 4, 2014

(65) Prior Publication Data
US 2015/0221001 A1    Aug. 6, 2015

(51) Int. Cl.
*G06Q 50/00* (2012.01)
*G06Q 30/02* (2012.01)
*G06Q 50/22* (2012.01)

(52) U.S. Cl.
CPC ......... *G06Q 30/0279* (2013.01); *G06Q 50/22* (2013.01)

(58) Field of Classification Search
CPC ...... G06Q 50/22; G06Q 50/24; G06F 19/322; G06F 19/30; G06F 19/327; G06F 19/3487
USPC ........................................................ 705/2–3
See application file for complete search history.

(56) References Cited

U.S. PATENT DOCUMENTS

| | | | |
|---|---|---|---|
| 7,792,705 B2* | 9/2010 | Bezos | G06Q 10/087 705/26.81 |
| 7,805,318 B1 | 9/2010 | Kuhn | |
| 8,443,005 B1* | 5/2013 | Goldman | G06Q 50/01 707/798 |
| 2001/0037218 A1 | 11/2001 | Kaker et al. | |

(Continued)

OTHER PUBLICATIONS

"Aidmatrix Enables Free Clinics to Serve Millions of Uninsured Patients", Global Logistics & Supply Chain Strategies, Dec. 17, 2007, 7 pages.

(Continued)

*Primary Examiner* — Reginald R Reyes
(74) *Attorney, Agent, or Firm* — Morrison & Foerster LLP

(57) ABSTRACT

Provided are methods, computer readable storage media, and systems for facilitating and receiving a donation of prescription medications through a peer-to-peer model. Exemplary methods include the steps of receiving registration information and a formulary from a recipient, receiving registration information from a donor, connecting the donor and recipient through communication of registration information, and verifying that the donor and recipient both approve a donation. Further methods include donation and recipient records for reconciling a medication donation. Other exemplary methods include the steps of providing a formulary to a medication donor, receiving registration information from a donor, approving the donor for donating a medication from the formulary, and receiving a donated medication, with further methods for reconciling and dispensing a donated medication. Computer readable storage media and computer-implemented systems including instructions for carrying out the described methods are also provided.

31 Claims, 15 Drawing Sheets

(56) References Cited

U.S. PATENT DOCUMENTS

| | | | |
|---|---|---|---|
| 2005/0071191 A1 | 3/2005 | Wilson et al. | |
| 2007/0233517 A1* | 10/2007 | Dayal | G06Q 50/22 705/2 |
| 2008/0301009 A1* | 12/2008 | Plaster | G06Q 10/087 705/28 |
| 2011/0257991 A1 | 10/2011 | Shukla | |
| 2013/0041675 A1* | 2/2013 | Cunningham | G06Q 50/22 705/2 |
| 2014/0279645 A1* | 9/2014 | Cohen | G06Q 30/0279 705/329 |

OTHER PUBLICATIONS

"Prescription Drugs Collection and Distribution", Agenda, Nov. 2012, p. 5.
"Beyond Waste", Jet Propulsion Laboratory, Jul. 20-22, 2012, 3 pages.
"Create an Account", Screenshots from www.SIRUM.org website, Jun. 28, 2011, 1 page.
"Donation Details", Screenshots from www.SIRUM.org website, Jun. 28, 2011, 1 page.
"Drug Repository Question & Answer Forum", Wisconsin Department of Health Services, Sep. 2010, pp. 1-3.
"Free Prescription Medications in Tulsa Oklahoma.", Tulsa Oklahoma free medications, Sep. 2010, 2 pages.
"Iowa Drug Donation Repository", IPDC Annual Report, 2009, 43 pages.
"Manage Medicine", Screenshots from www.SIRUM.org website, Jun. 28, 2011, 1 page.
"Shipping Label", Screenshots from www.SIRUM.org website, Jun. 28, 2011, 1 page.
"SIRUM: Supporting Initiatives to Redistribute Unused Medicine", 2:14 Minutes Video, Available at <https://www.youtube.com/watch?v=O193nVKGPZE>, Uploaded on Aug. 3, 2011, 2 pages.
"SIRUM: Supporting Initiatives to Redistribute Unused Medicine", Screenshots from YouTube video <https://www.youtube.com/watch?v=O193nVKGPZE>, Old Remove Patient Info, Aug. 3, 2011, 1 page.
"SIRUM: Supporting Initiatives to Redistribute Unused Medicine", Screenshots from YouTube video <https://www.youtube.com/watch?v=O193nVKGPZE>, Old Repackaging, Aug. 3, 2011, 1 page.
"Stanford Team Creates System to Recoup Unused Drugs", Available at <http://www.paloaltoonline.com/news/show_story.php?story_id=24457>, Feb. 27, 2012, 2 pages.
"Status Clinic POV", Screenshots from www.SIRUM.org website, Jun. 28, 2011, 1 page.
"Status Donor POV", Screenshots from www.SIRUM.org website, Jun. 28, 2011, 1 page.
"CAHF Quality Report Online", Dec. 2012, p. 9.
"Dashboard", Screenshots from www.SIRUM.org website, Jun. 28, 2011, 1 page.
"Dashboard : Recent Messages", Screenshots from www.SIRUM.org website, Jun. 28, 2011, 1 page.
Bill Silverfarb Daily Journal Staff, "Simitian's Bill to Expand Discarded Drug Program", The Daily Journal, Feb. 24, 2012, 1 page.
Birk, Susan, "Donations in Short Supply : Your Hospital's Unused Items can make a World of Difference", Charity, Dec. 2007, 2 pages.
CAHF, "Donating Surplus Medications : CAHF Members Work with SIRUM", E-News Sponsor, May 20, 2011, 2 pages.
Cohan, Peter, "SIRUM Gets Surplus Meds to the Poor", Forbes, Jul. 5, 2011, 2 pages.
Colliver, Victoria, "Connecting Unused Drugs, Uninsured Patients", Hearst Communications Inc., Mar. 2, 2012, 2 pages.
Opar, Alisa, "Rising Drug Costs Prompt New Uses for Old Pills", Nature Medicine, vol. 12, No. 12, Dec. 2006, p. 1333.
O'Reilly, Kevin B., "Charity Helps Medical Practices Donate Unused Drug Samples", Profession, Aug. 22, 2012, 3 pages.
Pelpola, Judith, "State Senator Unveils Bill at Haas Center", The Stanford Daily, Feb. 27, 2012, 4 pages.
San Jose Mercury News, "List of Donors and Recipients of Unused Pills could Grow if Bill Becomes Law", MercuryNews.com, Aug. 2012, 2 pages.
SIRUM, "Medicine Inventory", Screenshots from www.SIRUM.org website, Jun. 8, 2012, 1 page.
SIRUM, "Manifest", Screenshots from www.SIRUM.org website, Jun. 28, 2011, 1 page.
Spector, Rosanne, "Students' Plan for Unused Prescription Drugs Wins Approval from the Governor", Stanford Report, Oct. 19, 2005, pp. 1-2.
Stanford University, "We Promote Public Service Through Five Pathways. How do you Approach Public Service?", Commons : Uncommonly Good News from the Haas Center for Public Service, Jun. 2012, 12 pages.
Strom, Stephanie, "Old Pills Finding New Medicine Cabinets", The New York Times, May 18, 2005, pp. 1-2.
Wapner, Jessica, "Hurdles Facing Unused Prescription Drug Repositories : State-Legislated Programs for the Donation of Unused Drugs have seen Limited Success", Scientific American Magazine, Jan. 29, 2009, 2 pages.
Williams, Kiah, "SIRUM", Jun. 28, Jun. 2012, 2 pages.

* cited by examiner

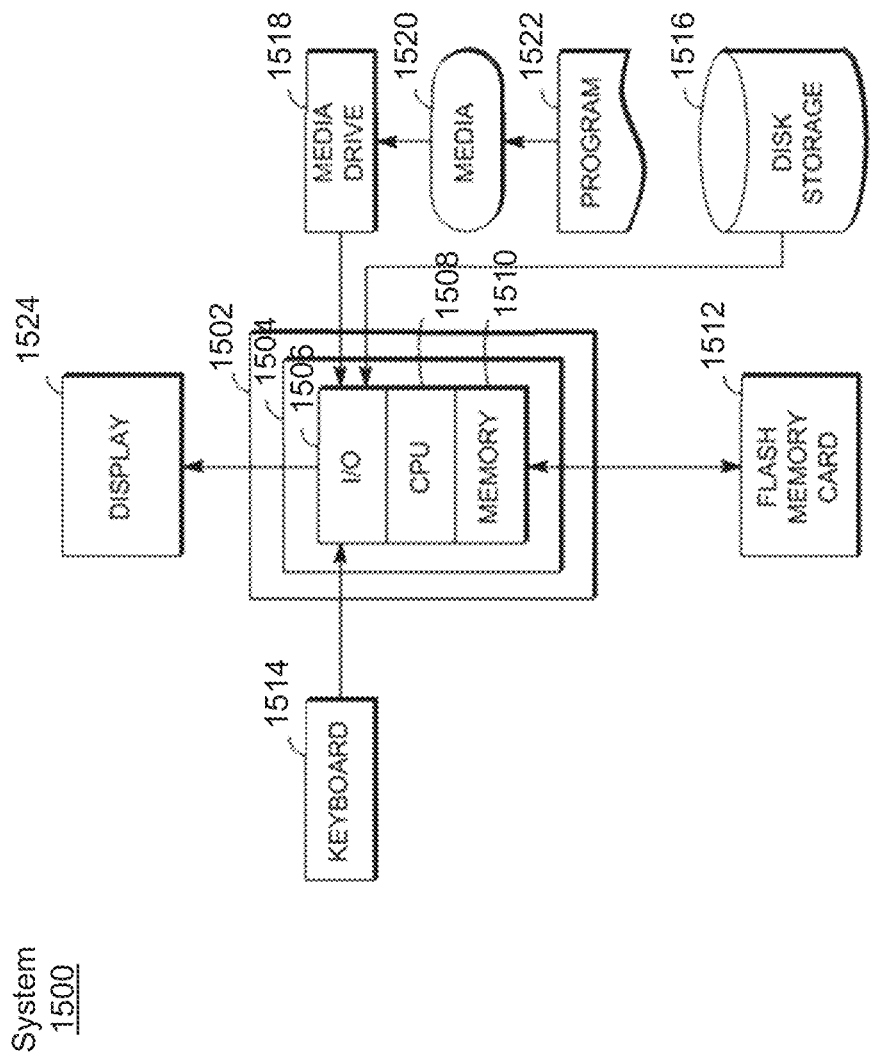

METHODS AND SYSTEMS FOR FACILITATING DONATION OF PRESCRIPTION MEDICATION

TECHNICAL FIELD

The present disclosure relates generally to facilitating the donation of prescription medications. More specifically, it relates to methods, systems, and computer readable storage media for facilitating and receiving a medication donation using a closed, peer-to-peer model.

BACKGROUND

Every day, drug manufacturers and care providers (such as hospitals, pharmacies and clinics) generate surplus or unused prescription medications. These may result from excess production or changes in the needs of a patient population. As a result, much of this excess medication expires and must be destroyed. In California alone, health facilities destroy an estimated $100 million worth of medications each year.

At the same time, health care costs continue to rise. Rising drug costs particularly impact uninsured patients who rely on safety-net clinics. Many of these patients forego medication due to cost. As such, a need exists to increase the supply of inexpensive medications by connecting safety-net clinics with the drug suppliers and dispensers that generate surplus medications. Providing these clinics with surplus medications also reduces the environmental and economic impacts of disposing of surplus medication.

Medication donation programs exist to enable drug suppliers and dispensers to donate their excess medications to clinics and individuals. However, existing models use a distributor as the intermediary between the medication donor and recipient. As the distributor must store donated medications before shipping them to a recipient, maintaining a licensed distributor requires costly overhead charges to ensure drug safety and security while also providing for medication storage and shipping.

Therefore, a need exists for a more efficient medication redistribution model for medication donation. A peer-to-peer model would avoid costly overhead and increase efficiency by directly connecting medication donors and recipients. In order to provide medication donors with the same quality and safety assurances that a distributor typically provides, a need exists for methods of instituting a closed system for peer-to-peer medication redistribution. Such a closed peer-to-peer system would enhance cost efficiency for donation facilitators and recipients while maintaining the proper safety, legal, and security standards that medication donors require.

BRIEF SUMMARY

To meet this demand, the implementations described below provide methods and systems for facilitating peer-to-peer medication redistribution. These methods and systems provide a closed, peer-to-peer system for facilitating or receiving a medication donation. They allow the medication donor and medication recipient to connect and carry out a donation directly, while also assuring that the donation is done safely and in accordance with the policies of the medication donor/recipient. Methods for reconciling and accounting for each medication in a donation are provided. Computer readable storage media and computer systems for carrying out any of the methods described above are also provided.

In accordance with some implementations, a method for facilitating the donation of a medication is provided. The method may include receiving recipient information from a medication recipient, including registration information and a formulary of medication(s); receiving donor information from a medication donor, including registration information; connecting the medication donor to the medication recipient by at least one or both of providing the donor information to the recipient and providing the recipient information to the donor; and verifying that the medication donor has approved donating a medication from the formulary to the medication recipient, and that the medication recipient has approved receiving a medication from the formulary from the medication donor.

In some implementations, the methods further include verifying the medication donor as eligible to donate a medication from the formulary, the medication recipient as eligible to receive a medication from the formulary, or both.

In some implementations, the methods further include receiving a donation record from the medication donor, where the donation record includes a list of the name and quantity of each medication to be sent by the medication donor to the medication recipient. In some implementations, the donation record may be stored as an electronic record on a computer with a processor and memory. In some implementations, the donation record is provided to the medication recipient.

In some implementations, the methods further include receiving a recipient record from the medication recipient, where the recipient record includes a list of the name and quantity of each medication received by the medication recipient. In some implementations, a recipient record may further indicate how each of the received medication(s) was handled by the medication recipient. In some implementations, the recipient record may be stored as an electronic record on a computer with a processor and memory. In some implementations, the recipient record is provided to the medication donor.

In accordance with some implementations, a method for receiving a donated medication is provided. The method may include providing a formulary listing one or more medications to a medication donor; receiving registration information from the medication donor; approving the medication donor for donating a medication from the formulary; and receiving at least a portion of the medication(s) from the formulary from the medication donor.

In some implementations, the methods include creating a recipient record, as described above. In some implementations, the recipient record may be stored as an electronic record on a computer with a processor and memory. In some implementations, the recipient record is provided to the medication donor.

In some implementations, the methods include dispensing a donated medication, which may involve receiving a valid prescription for the donated medication from a patient; verifying the legal eligibility of the patient to receive the donated medication; labeling the donated medication; and dispensing the labeled, donated medication to the patient.

In accordance with some implementations, a computer readable storage medium with instructions is provided. These instructions may allow receiving recipient information from a medication recipient, including registration information and a formulary of medication(s); receiving donor information from a medication donor, including registration information; connecting the medication donor to the medication recipient by at least one or both of providing the donor information to the recipient and providing the recipient information to the donor; and verifying that the medication donor has approved donating a medication from the formulary to the medication recipient, and that the medication recipient has approved receiving a medication from the formulary from the medication donor.

In accordance with some implementations, a system with a processor and memory that includes instructions is provided. These instructions may allow receiving recipient information from a medication recipient, including registration information and a formulary of medication(s); receiving donor information from a medication donor, including registration information; connecting the medication donor to the medication recipient by at least one or both of providing the donor information to the recipient and providing the recipient information to the donor; and verifying that the medication donor has approved donating a medication from the formulary to the medication recipient, and that the medication recipient has approved receiving a medication from the formulary from the medication donor.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 15 illustrates a typical computing system that may be employed to implement some or all processing functionality in certain implementations.

DETAILED DESCRIPTION

Figure 1:
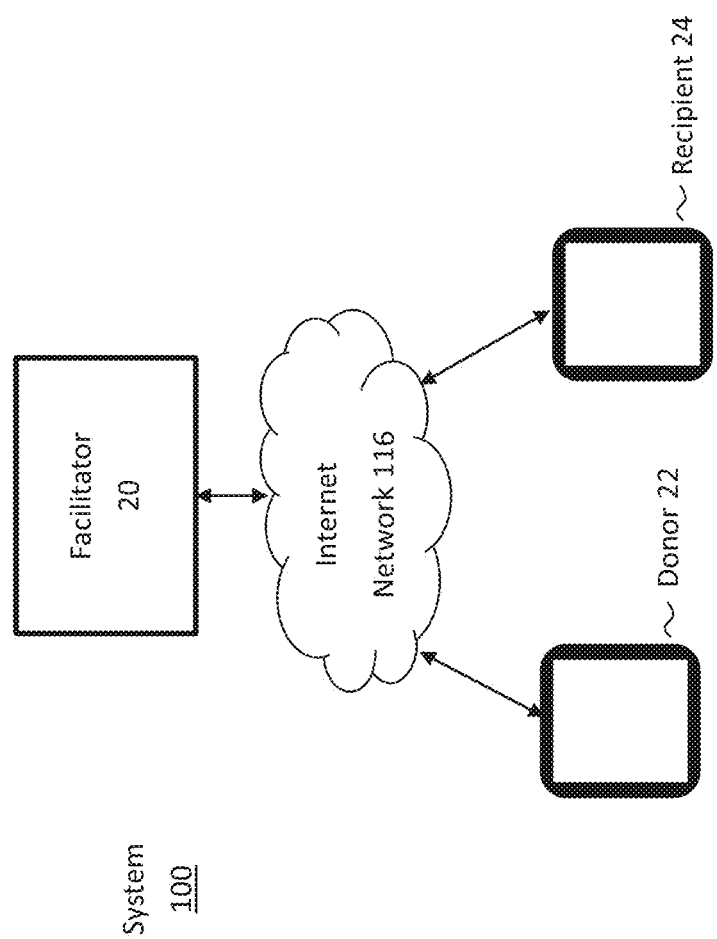
FIG. 1 illustrates an exemplary environment for some systems and processes for facilitating peer-to-peer redistribution of donated medication, in accordance with some implementations.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

According to certain aspects of the present disclosure, methods and systems are provided for facilitating or receiving a medication donation. As used herein, the terms donation/donate and redistribution/redistribute may be used interchangeably. A medication donation may refer to the transfer of a medication from a donor to a recipient. In some implementations, the terms donation/donate may refer to giving a medication to a recipient in-kind without fee. In some implementations, the terms donation/donate may include providing a medication to a recipient in exchange for a nominal payment, such as a payment at less than market cost. In some implementations, the terms donation/donate may refer to receiving a medication in exchange for a fixed "membership" fee paid by the donor or recipient, or a fee based on usage rather than discrete donations and/or medications (e.g., charging a fee based on the number of donors in the system, number of donations made, etc.).

As used herein, a medication donor may refer to an entity eligible under applicable state and/or federal law to donate a medication, or a third-party contracted with the entity to provide services on the entity's behalf. Examples of medication donors may include manufacturers, wholesalers, hospitals, clinics, health facilities, assisted living facilities, and pharmacies. As used herein, a medication recipient (the term "donee" may be used interchangeably) may refer to an entity eligible under applicable state and/or federal law to receive and dispense a medication, or a third-party contracted with the entity to provide services on the entity's behalf. Examples of medication recipients may include clinics (e.g., safety-net clinics), pharmacies, dispensaries, drug outlets, and individuals. As used herein, a facilitator of a medication donation may relate to an entity providing information on behalf of the medication donor and/or medication recipient that enables the medication donation to occur. In some implementations, the facilitator may be a non-profit entity for medication redistribution, for example a §501(c)(3) charitable organization as defined by the United States tax code. In some implementations, the facilitator may be a non-profit or for-profit health care provider, for example a pharmacy or clinic, or a third-party technology platform.

Initially, and with reference to FIG. 1, an exemplary environment in which certain aspects and examples of the systems and processes described herein may operate. Generally, a client (e.g., a medication donor) device 22 may access a server 20, e.g., a server system associated with a facilitator, which includes or accesses logic for performing one or more exemplary processes described, e.g., receiving recipient or donor information, approving the medication donor or recipient as eligible to donate or receive a medication, or connecting the medication donor to the medication recipient, causing the display of interfaces for the client device, and so on. Server 20 and clients 22 and 24 (e.g., a medication recipient) may include any one of various types of computer devices, having, e.g., a processing unit, a memory (which may include logic or software for carrying out some or all of the functions described herein), and a communication interface, as well as other conventional computer components (e.g., input device, such as a keyboard/touch screen, and output device, such as display). For example, clients 22 and 24 may include a desktop computer, mobile device such as a mobile phone, web-enabled phone, or smart phone.

Client 22 and server 20 may communicate, e.g., using suitable communication interfaces via a network 116, such as a Local Area Network (LAN) or the Internet. Client 22 and server 20 may communicate, in part or in whole, via wireless or hardwired communications, such as Ethernet, IEEE 802.11b wireless, or the like. Additionally, client 22 and server 20 may communicate, e.g., using suitable communication interfaces, via a second network, such as a mobile/cellular network. Communication between client 22 and server 20 may further include or communicate with various servers such as a mail server, mobile server, media server, telephone server, and the like.

One or both of client 22 and server 20 generally includes logic (e.g., http web server logic) or is programmed to format data, accessed from local or remote databases or other sources of data and content, for providing and/or receiving information via network 118 according to various examples described herein. To this end, server 20 may utilize various web data interface techniques such as Common Gateway Interface (CGI) protocol and associated applications (or "scripts"), Java® "servlets", i.e., Java® applications running on server 20, or the like to present information and receive input from client 22. The server 20, although described herein in the singular, may actually comprise plural computers, devices, databases, associated backend devices, and the like, communicating (wired and/or wireless) and cooperating to perform some or all of the functions described herein. Server 20 may further include or communicate with account servers (e.g., email servers), mobile servers, media servers, and the like.

It should be noted that although the exemplary methods and systems described herein describe use of a separate server and database systems for performing various functions, other embodiments could be implemented by storing the software or programming that operates to cause the described functions on a single device or any combination of multiple devices as a matter of design choice so long as the functionality described is performed. Similarly, the database system described can be implemented as a single database, a distributed database, a collection of distributed databases, a database with redundant online or offline backups or other redundancies, or the like, and can include a distributed database or storage network and associated processing intelligence. Although not depicted in the figures, server 20 (and other servers and services described herein) generally include such art recognized components as are ordinarily found in server systems, including but not limited to processors, RAM, ROM, clocks, hardware drivers, associated storage, and the like. Further, the described functions and logic may be included in software, hardware, firmware, or combination thereof.

Figure 2:
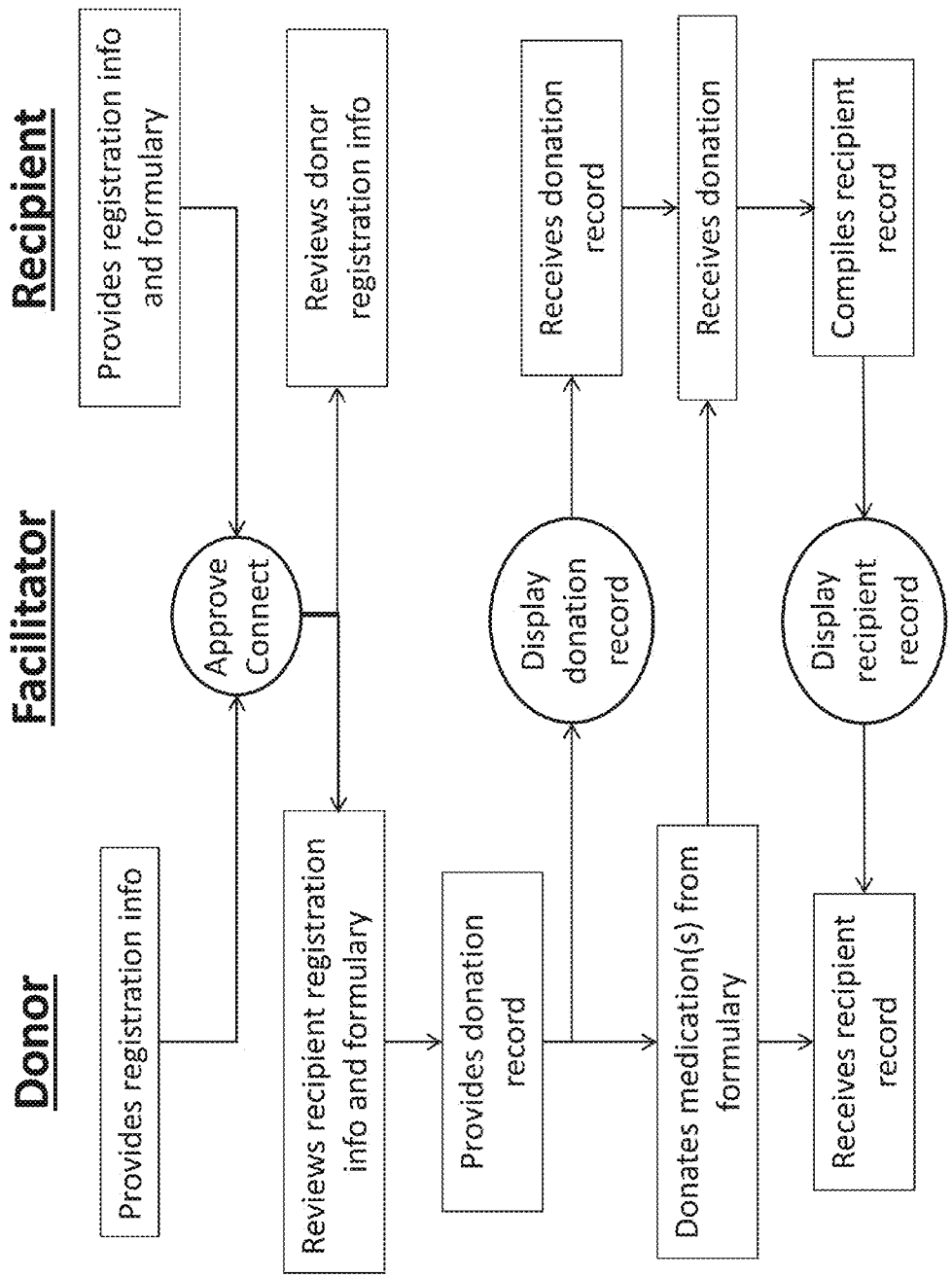
FIG. 2 is a flow chart illustrating a method for facilitating peer-to-peer redistribution of donated medication, in accordance with some implementations.

FIG. 2 illustrates a flow chart for an exemplary method of facilitating the donation of a medication, according to some implementations. This example illustrates some aspects and implementations for a closed, peer-to-peer model for the redistribution of a medication. The closed, peer-to-peer model allows medication donations to take place securely between registered medication donors and recipients. As used herein, the term peer-to-peer refers to direct exchange of a donation and/or information between a medication donor and a medication recipient without a medication distributor (i.e., an intermediary that directly ships and/or stores the donated medication). These methods may include an intermediary facilitator that collects information from medication donors and recipients, moderates their interactions by providing information only to registered users, and allows medication donors and recipients the ability to update their information, inventory, and/or preferences with respect to prospective donors/recipients.

Figure 3:
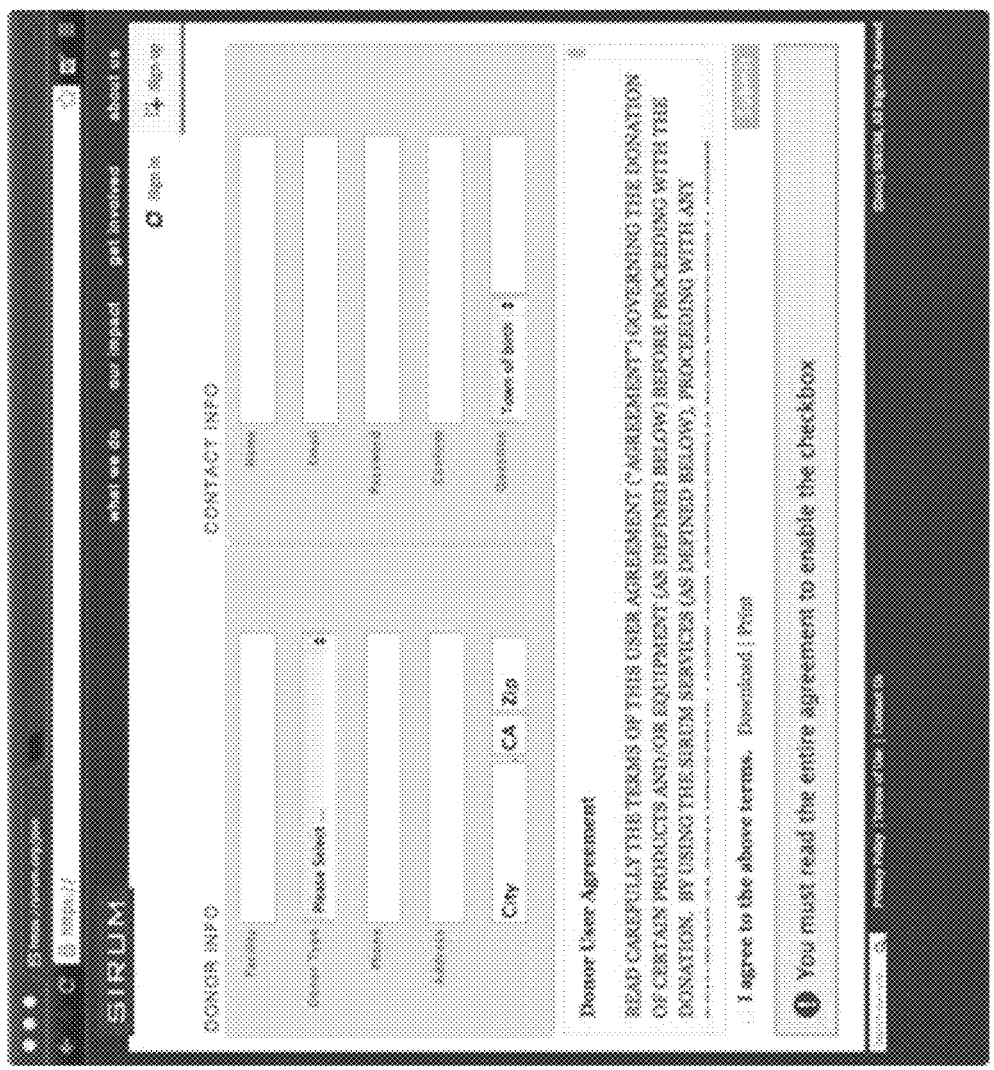
FIG. 3 is a screenshot illustrating donor registration for a medication donation using an Internet-based platform, in accordance with some implementations.
Figure 4:
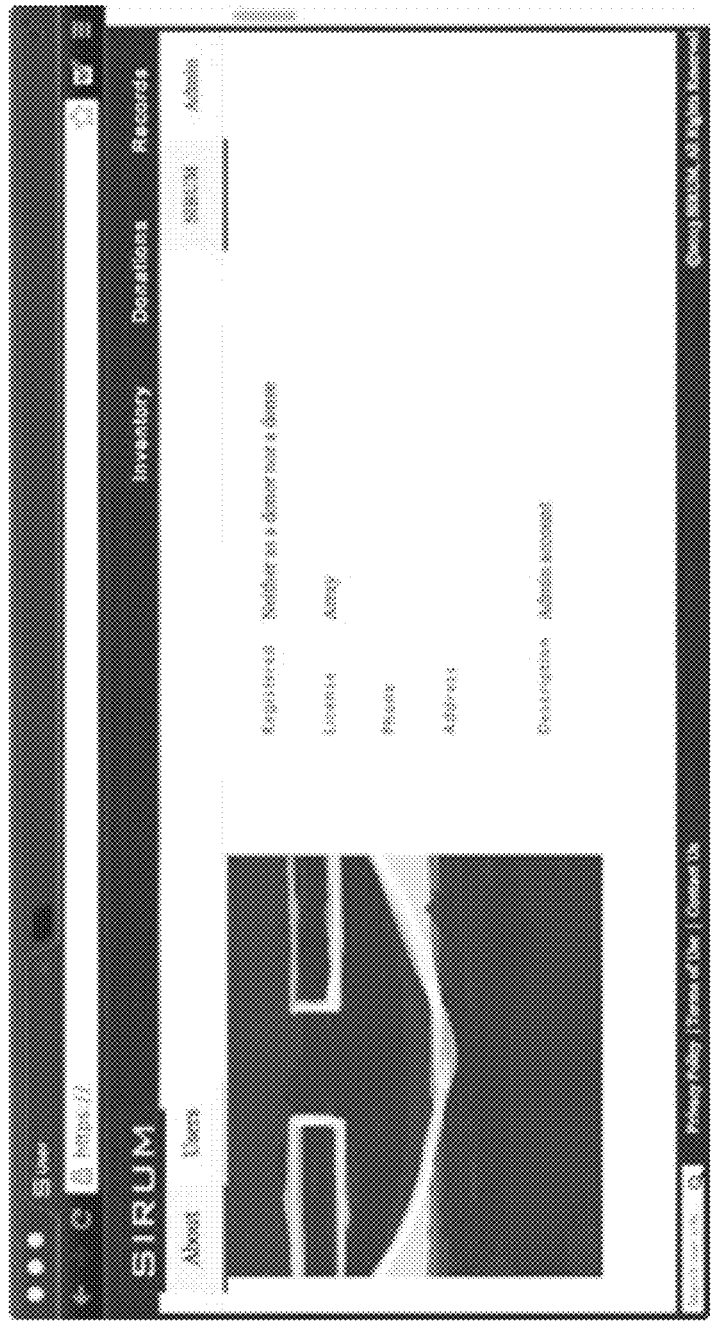
FIG. 4 is a screenshot illustrating donor information provided by an Internet-based platform, in accordance with some implementations.

In the example illustrated in FIG. 2, a medication donor provides registration information to the facilitator. FIG. 3 illustrates an implementation of this step, using an Internet-based platform to obtain and/or store donor information. As used herein, registration information, for the medication donor or the recipient, may include the entity name, address, and license type. In some implementations, a medication recipient similarly provides registration information to the facilitator. An implementation of registration information is provided in FIG. 4, which shows an exemplary entry with registration information, including the entity name, license type, phone number, and address.

In some implementations, registration information may include any information sufficient to determine whether the medication donor is eligible to donate a medication. In some implementations, eligibility may refer to legal eligibility. Determining the eligibility of a medication donor to donate a medication may include several steps. Legal eligibility is currently governed by the statutes and regulations of each state, as well as any applicable federal laws. State regulations may be published, for example, by the state Department of Public Health and/or the state Board of Pharmacy. These statutes and regulations differ, but typically they may specify one or more license types as eligible to donate a particular type of medication. By way of example, one method of determining if a medication donor is eligible to donate a medication may be through consulting the appropriate state statutes and regulations to see which license type(s) may be permitted to donate the medication, and then determining whether the medication donor has a permitted license type using the donor information. One may also check whether the address listed on the license matches the address provided in the donor information. If an individual's name is listed in the donor information, one may also verify with the medication donor that the listed individual is authorized to act on its behalf. Some medication donors/recipients, e.g., health care providers, may only authorize a subset of employees to arrange a medication donation.

In some implementations, the donor and/or recipient registration information may be stored as an electronic record, wherein the electronic record is stored on a computer with a processor and memory. In particular, the computer processor may be configured to establish the electronic record in response to input from the medication donor and/or recipient and, in some implementations, transmit the electronic record to the facilitator, medication donor, or medication recipient. The computer memory may be configured to store the electronic record and/or any instructions for the processor necessary to carry out the desired processor functions.

Figure 5:
FIG. 5 is a screenshot illustrating a recipient formulary provided by an Internet-based platform, in accordance with some implementations.

In some implementations, a medication recipient also provides a formulary. FIG. 5 illustrates an exemplary embodiment of a formulary as provided by an Internet-based platform. As used herein, a formulary refers to a list that communicates one or more medications sought to be received from the medication donor. The formulary may positively list one or more medications sought to be received, or it may list them negatively (e.g., any medication except for listed medication(s)), as described below. In some implementations, a formulary may include a list of all medications eligible for donation. In some implementations, a formulary includes a list of the name, strength, and dosage form of any medication(s) accepted by the medication donor (see entry for "Albuterol sulfate" in FIG. 5). A formulary may also include whether a medication is brand-name or generic. A formulary may also include medication expiration dates or a minimum amount of time that a medication will be accepted before its expiration date. A formulary may also include minimum and/or maximum quantities of each drug that will be accepted, and it may include an inventory listing how much of each medication is desired compared to the current stock (see column for "Remaining" in FIG. 5).

In addition to, or instead of, listing accepted medications, a formulary may include a list of medication(s) not accepted by the medication recipient. In some implementations, a formulary could be defined by what is not acceptable, rather than positively listing which medication(s) are acceptable. For example, a formulary could list any/all non-controlled drugs, in which case the recipient would accept any drug without a Drug Enforcement Agency Schedule. In some implementations, medications accepted and not accepted will be suitably marked within the formulary so as to distinguish them and convey their acceptability to potential medication donors and/or the facilitator.

In some implementations, the list of medications as provided by the formulary may be grouped, either by the facilitator or the medication recipient. This list may include both accepted and non-accepted medications. The list of medications may be grouped, for example, by national drug code (NDC), active ingredient, brand name, therapeutic area, controlled substance schedule, dosage form, handling requirements (e.g., requires refrigeration), drug class, or by any combination thereof.

In some implementations, the formulary may be reviewed by the facilitator or donor to verify that each listed medication is eligible for donation, and any medication(s) not eligible may be removed. Medications not eligible for donation will vary according to federal law and state statutes and regulations, but these may include, e.g., controlled substances and drugs that require special registration with the manufacturer. Other medications not eligible for donation may include medications for which it may be difficult for the medication facilitator or recipient to ensure that they would be shipped under suitable conditions, e.g., medications that require refrigeration. In some implementations, the medication recipient may be responsible for ensuring that each medication on the formulary is legally eligible for donation.

Referring back to FIG. 2, the facilitator may verify the medication donor as eligible to donate a medication from the formulary, the medication recipient as eligible to receive a medication from the formulary, or both, in accordance with some implementations. Verification may include verification of the legal eligibility of the medication donor/recipient to donate/receive a medication from the formulary. For example, registration information (e.g., license type) from the medication donor/recipient may be used to determine whether the donor/recipient is eligible to donate/receive a medication under any and all applicable statutes and regulations, as described above. In some embodiments, the facilitator may share the formulary, but without the medication recipient's registration information, to registered medication donor(s) for their review, selection, or approval prior to being connected with the medication recipient.

As illustrated in FIG. 2, the facilitator connects the medication donor to the medication recipient by at least one or both of providing the donor information to the recipient and providing the recipient information to the donor, in accordance with some implementations. The registration and approval steps create a secure, closed environment for medication donation that includes registered and/or approved donors and recipients. The connecting step establishes a peer-to-peer connection through which a medication donation may be facilitated. By providing the recipient information to the donor, the medication donor may review the recipient name and address required for shipping a donation and may review the formulary listing the medication(s) acceptable or desired for donation. By providing the donor information to the recipient, the recipient may review the source of the donation and can identify the donation when it is shipped.

Figure 6:
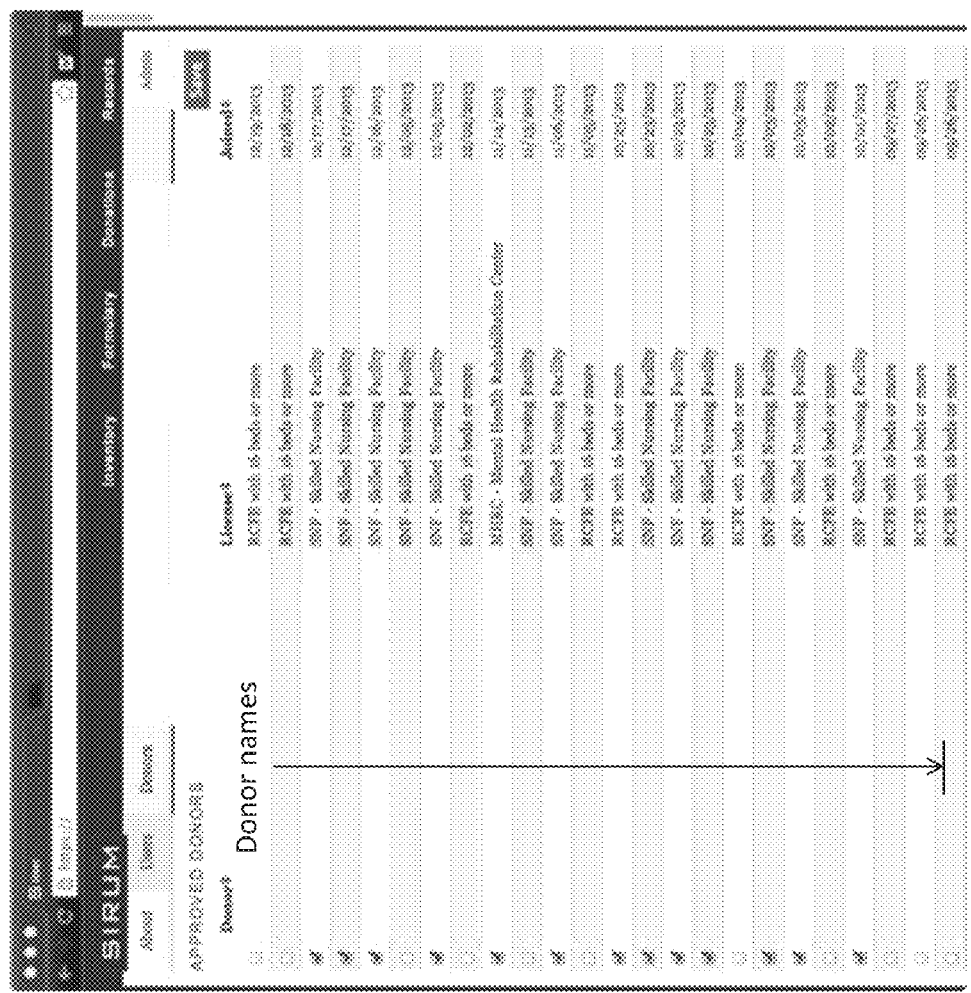
FIG. 6 is a screenshot illustrating the selection of approved medication donors using an Internet-based platform, in accordance with some implementations. Medication donor names have been removed.

In some implementations, the facilitator may connect the medication donor to the medication recipient by displaying a list of registered medication donors/recipients and allowing the medication donors/recipients to select a party for donating/receiving a medication. As illustrated in FIG. 6, the connecting step may take place via an Internet-based platform accessible to registered medication donors and recipients, according to some implementations. FIG. 6 shows that a medication recipient may approve one or more medication donors after viewing donor registration information, such as donor name and license type. In some implementations, the formulary may be provided only to a registered medication donor, for example a medication donor that has provided registration information.

By connecting the medication donor and medication recipient and requiring joint approval, each party is able to independently review the other party for aspects such as the entity's mission, reputation, overlap of surplus medication and the formulary, and geographic proximity. Each party's registration information provided to the facilitator may be verified by the other party using publically available information, e.g., government websites, press, regulatory surveys, and citations. In this way, each party may be able to confirm that the other exists, is operational, has a valid license, has provided correct address and license information (for example, that the license address matches the shipping address provided by the medication recipient), is eligible to donate/receive the desired medication(s) under its license type according to applicable statutes and regulations, and is competent to address any safety or storage issues associated with the particular type of medication to be donated or received. After connecting the medication donor and medication recipient, the medication donor may then use the medication recipient's information to ship a donation of one or more medications, for example by direct pickup, a private courier, common carrier, or the postal service.

In some implementations, the facilitator verifies that the medication donor has approved donating a medication from the formulary to the medication recipient, and that the medication recipient has approved receiving a medication from the formulary from the medication donor. In some implementations, the medication donor and/or medication recipient are directly solicited to approve one another. In some implementations, this approval may be explicitly stated on paper or in an electronic form. In some implementations, this approval may be implicit in providing a shipping label, courier pickup, sending a donation, accepting a donation, and/or providing a donation/recipient record. In some implementations, the medication recipient may approve the donation by providing a recipient record.

Upon sending the donation and, optionally, receiving a recipient record (see below for description of recipient records), the medication donor may, in some implementations, compile a donation record. The donation record may be generated by the facilitator or the medication recipient, to be filled in by the medication donor or it may be generated by the medication donor itself. The donation record may be compiled de novo, or it may be created by altering the recipient record. As used herein, the donation record may include a list of the name and quantity of each medication to be sent by the medication donor to the medication recipient, an example of which is shown in FIG. 2.

Figure 7:
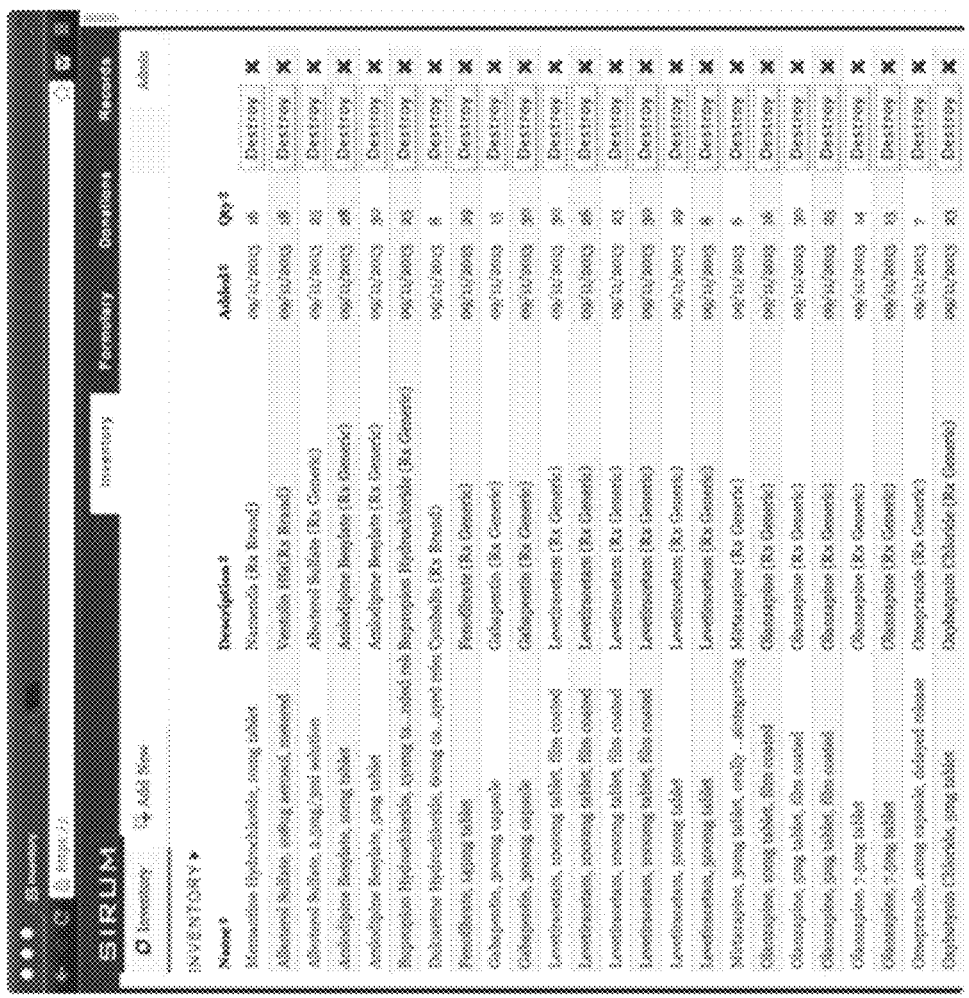
FIG. 7 is a screenshot illustrating an inventory of donor medication for potential donation using an Internet-based platform, in accordance with some implementations.

FIG. 7 illustrates an implementation of a donation record using an Internet-based platform for obtaining and storing the record. For example, the implementation shown in FIG. 7 displays the active ingredient, strength, dosage form, brand/generic type, date added, and quantity for each medication in a donation. In some implementations, the donation record may include the tracking number for the donation shipment. In some implementations, clicking on a medication could bring up additional information, e.g., a picture or description of its size, shape, or color. It also displays a status identifier (e.g., labeled "Destroy" in FIG. 7) that can be added by the medication recipient as part of the recipient record. In some implementations, the facilitator provides the donation record to the medication recipient.

Figure 9:
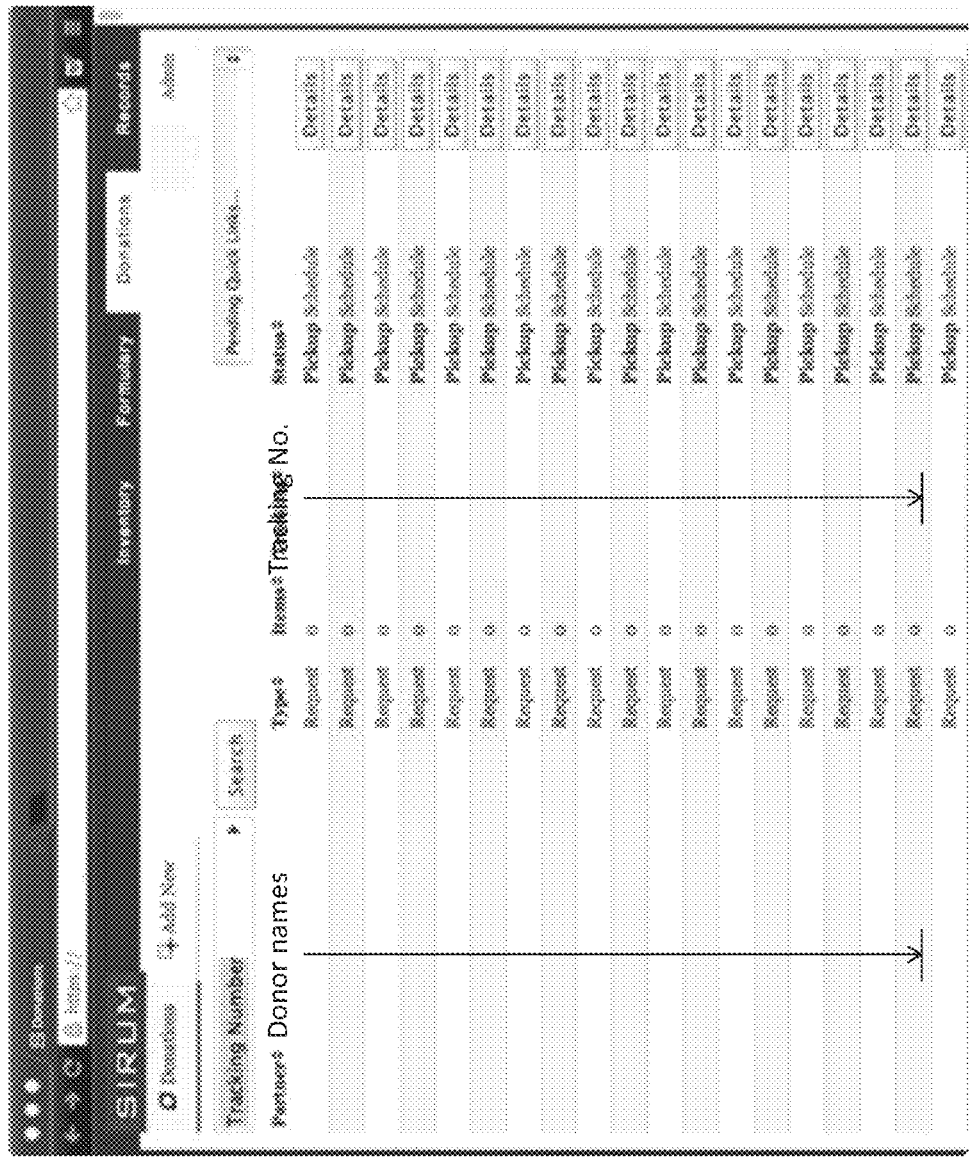
FIG. 9 is a screenshot illustrating a series of medication donations provided by an Internet-based platform, in accordance with some implementations. Medication donor names have been removed.

In some implementations, the donation record may be stored as an electronic record, wherein the electronic record is stored on a computer with a processor and memory. Referring back to FIG. 2, the facilitator may display or otherwise provide the donation record to the medication recipient. FIG. 9 illustrates an Internet-based platform for displaying pending and previously executed donation records to the medication recipient, according to some implementations.

In particular, the computer processor may be configured to establish the electronic record in response to input from the medication donor and, in some implementations, transmit the electronic record to the facilitator and/or the medication recipient. This electronic record may be generated de novo, or it may be a version of the recipient record updated by the medication donor using the computer processor and memory. The computer memory may be configured to store the electronic record and/or any instructions for the processor necessary to carry out the desired processor functions.

Figure 8:
FIG. 8 is a screenshot illustrating a shipping label and donation instructions for a medication donation provided by an Internet-based platform, in accordance with some implementations.

As shown in FIG. 2, according to some peer-to-peer implementations of the disclosed methods, the medication donor directly ships a medication donation to the medication recipient. This step does not require that the facilitator handles or stores the medication donation; rather, the medication donor and medication recipient may independently arrange for shipping. In some implementations, the facilitator or medication recipient may provide a shipping label to the medication donor suitable for shipping the medication to the medication recipient. As illustrated in FIG. 8, the shipping label includes the medication recipient address and other information necessary to ship the donation, for example by a private courier, common carrier, or the postal service. Instructions for handling the donation may further be provided with the shipping label. In addition, the facilitator or medication recipient may also provide a suitable container for shipping the donation. In some implementations, the shipping label or shipping container may be distinctively marked to allow the medication recipient to easily identify the donation shipment. As many clinics and other care providers receive numerous shipments each day, this distinctive marking may facilitate the donation by allowing for quick and easy identification. In some implementations, before or after completion of a first donation, the facilitator or medication recipient may arrange carrier pickup for a subsequent donation from the medication donor to the medication recipient. Any subsequent pickup(s) between the two parties may be arranged on a regular or as-needed basis.

Upon receiving the donation (and, optionally, a donation record), the medication recipient may, in some implementations, compile a recipient record. The recipient record may be generated by the facilitator or the medication donor, to be filled in by the medication recipient, or it may be generated by the medication recipient itself. The recipient record may be compiled de novo, or it may be created by altering the donation record. As used herein, the recipient record may include the name and quantity of each medication received in the medication donation. In some implementations, the recipient record may be generated by the facilitator or medication recipient upon receipt of a donation, then sent to the medication donor and/or facilitator. In some implementations, the recipient record is a version of a donation record that is annotated to reflect which medication(s) were received, and which, if any, were not received, then sent back to the medication donor and/or facilitator.

In some implementations, the recipient record may further include a status entry for each of the received medication(s). As used herein, a status entry may indicate how the received medication was handled by the medication recipient, which may be based, in part, on the condition of the medication and the needs of the medication recipient. As used herein, examples of suitable status entries may include "accepted," "rejected," "dispensed," "returned to donor," "transferred," "reverse distributed," and "destroyed." FIG. 7 illustrates an exemplary status identifier ("Destroy") that may be added to a recipient record by the medication recipient, according to some implementations.

Ideally the items and quantities in the recipient record will match the donation record. However, if applicable, the recipient record may further include the name and quantity of each medication received in the donation that was not listed in the donation record. The recipient record may also include the name and quantity of each medication from the donation record that was not received by the medication recipient, if applicable. The recipient may also record a different quantity than the donor for a particular item, if applicable. As described before, in some implementations, the recipient record is provided to the medication donor by the facilitator or the medication recipient. In this way, the recipient record may help create the donation record, or to reconcile the donation and the inventories of both the medication donor and medication recipient.

Figure 10:
FIG. 10 is a screenshot illustrating a recipient record provided by an Internet-based platform, in accordance with some implementations. Various features of the recipient record are illustrated: (A) a list of medications received in the medication donation; (B) a list of both the donor-reported and recipient-reported quantities for items in the donation; (C) a check box signifying how the recipient handled each medication; (D) a dialog box for adding an additional type of medication received in the donation; and (E) the shipment tracking number, shipment status, and date of verification for the medication donation.

FIG. 10 illustrates an exemplary recipient record provided by an Internet-based platform, according to some implementations. In this implementation, the name, strength, and dosage form of each medication is listed (identified in FIG. 10A). The quantity of each medication received by the recipient (identified in FIG. 10B) is also listed. In some implementations, a zero recipient quantity signifies that the recipient did not receive an item recorded by the donor, and a zero donor quantity signifies that the recipient received an item not recorded by the donor. These steps may help to identify and reconcile potential discrepancies in medication type and/or quantity. FIG. 10C shows checkboxes used as status indicators of whether the recipient accepted or rejected each medication. Any additional medication received may be added to the recipient record, for example through the "Add New" dialog box pointed out by FIG. 10D. Any medication not received may be removed from the recipient record. The recipient record may also include a tracking number and/or the date of verification, as shown by FIG. 10E.

In some implementations, the recipient record may be stored as an electronic record, wherein the electronic record is stored on a computer with a processor and memory. In particular, the computer processor may be configured to establish the electronic record in response to input from the medication recipient and, in some implementations, transmit the electronic record to the facilitator and/or the medication donor. This electronic record may be generated de novo, or it may be a version of the donation record updated by the medication recipient using the computer processor and memory. The computer memory may be configured to store the electronic record and/or any instructions for the processor necessary to carry out the desired processor functions.

Figure 11:
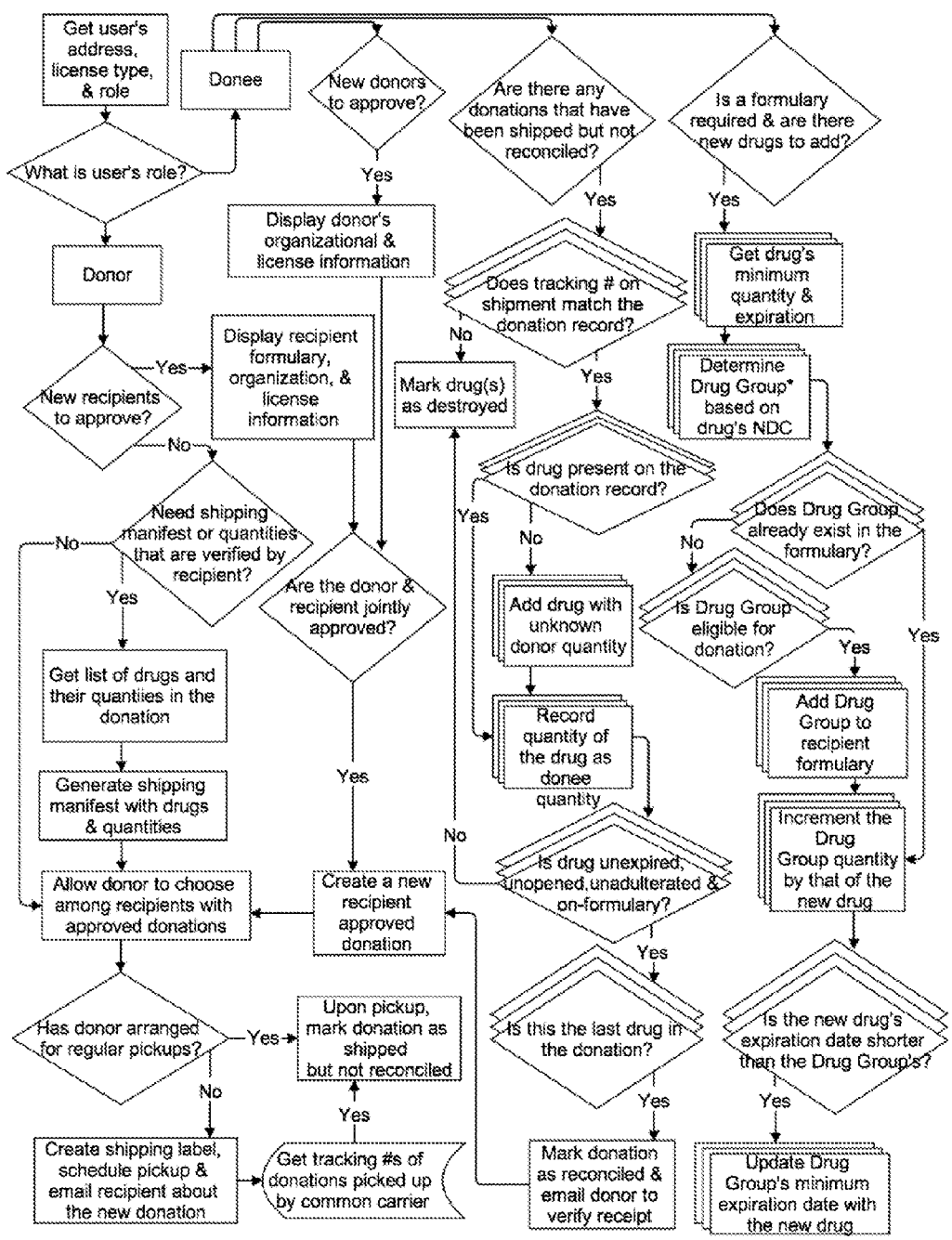
FIG. 11 is a flow chart illustrating an Internet-based method for facilitating peer-to-peer redistribution of donated medication, in accordance with some implementations.

FIG. 11 provides a flow chart for an Internet-based platform that accomplishes many of the methods and steps described herein. As many of the methods and implementations described herein involve compiling, storing, and communicating information, such as registration information and donor and recipient records, an Internet-based platform may be highly advantageous. In some implementations, the facilitator may develop, host, and/or maintain the Internet-based platform. In some implementations, the medication recipient may develop, host, and/or maintain the Internet-based platform. One of skill in the art would also recognize that all of the methods described herein could be accomplished without an Internet-based platform, using standard electronic or other means for communication and documentation.

In some implementations, the facilitator and/or medication recipient may be allowed to block the medication donor for subsequent medication donation(s) to the medication recipient. Reasons for blocking the medication donor may include providing incorrect or unsuitable medications (e.g., expired, adulterated, or damaged medications), providing incorrect registration information (e.g., an address that does not match the medication donor license), a regulatory citation or non-compliance, or general unresponsiveness or incompetence in shipping a donation. In this way, medication recipients may be more likely to receive reliable and high-quality donations in the future by eliminating unsuitable medication donors.

As described above, certain aspects of the present disclosure relate to facilitating a donation between a medication donor and a medication recipient. Some of these methods may include a facilitator who arranges and documents the donation without physically receiving the donation. It will be appreciated by one of skill in the art, however, that these methods and systems are equally useful to a medication recipient who uses them to facilitate a donation to itself, for example without the use of a facilitator.

Figure 12:
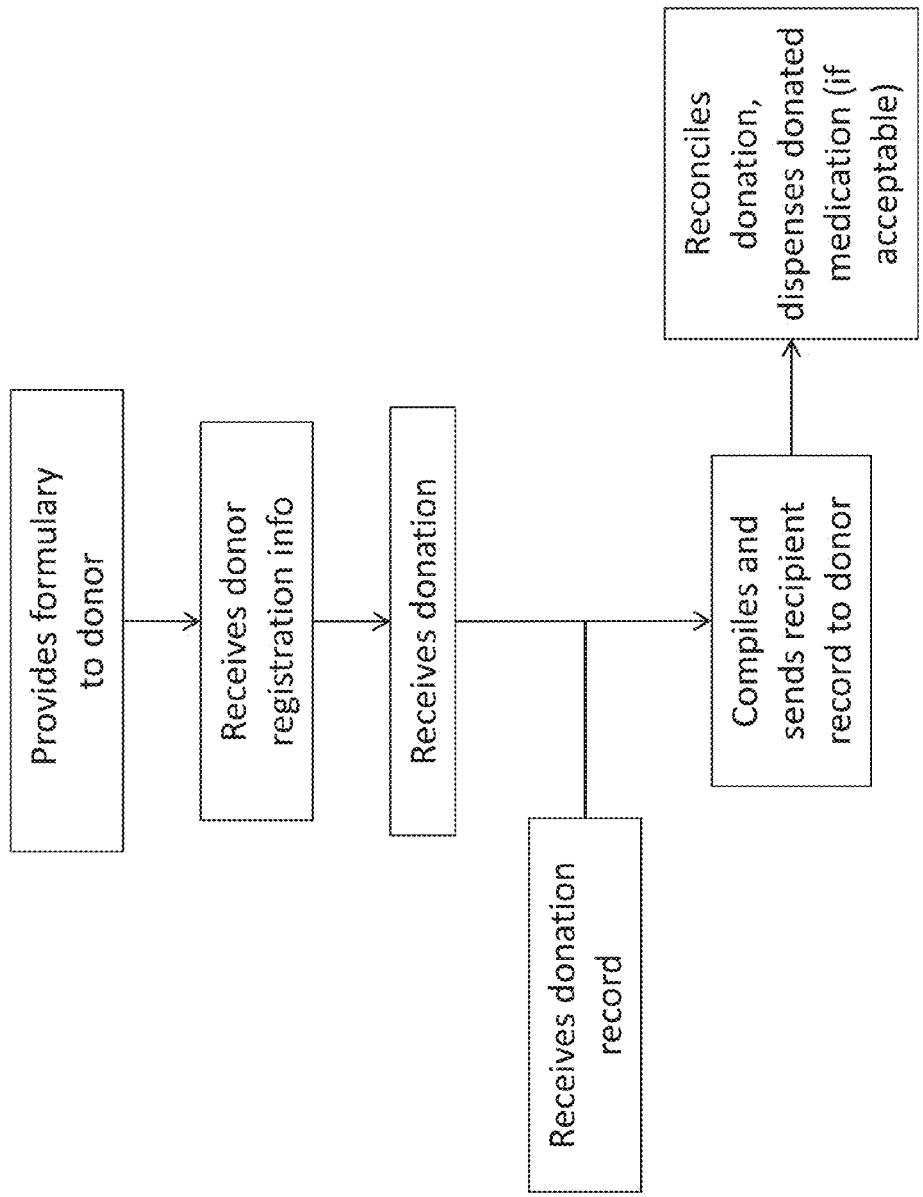
FIG. 12 is a flow chart illustrating a method for receiving a donated medication, in accordance with some implementations.

FIG. 12 illustrates a method for receiving a donated medication, according to some implementations. In some implementations, the medication recipient provides a formulary, as described above, to the medication donor. This is advantageous for the medication recipient because, unlike relying upon an at-will donation by the medication donor, the medication recipient informs the medication donor of its needs through the formulary. As discussed above, the formulary may relay to the medication donor the type of desired medication(s) name and strength, brand-name or generic, expiration dates or a minimum amount of time that a medication will be accepted before its expiration date, minimum and/or maximum quantities of each drug that will be accepted, any remaining medication need(s) relative to the quantity as listed in the formulary before the donation, and any medication(s) not accepted by the medication recipient.

In some implementations, the medication recipient receives donor information, as described above. This allows the recipient to evaluate the medication donor, for example by determining its eligibility (e.g., legal eligibility) to donate a medication from the formulary. In some implementations, the medication recipient may approve the medication donor for donating the one or more medications from the formulary. In some implementations, this may include determining the eligibility (e.g., legal eligibility) of the medication donor to donate the medication(s), as described above. In some implementations, the medication recipient may receive one or more donated medications from the formulary. The medication recipient may further receive a donation record, as described above, and compile and send a recipient record to the medication donor, as described above.

In some implementations, the medication donor may receive recipient information, as described above. The donor may then evaluate the medication recipient, for example by determining its eligibility to receive a medication from the formulary. In some implementations, the medication donor may then donate one or more medications from the formulary. The medication donor may also receive a recipient record, as described above, and compile and provide a donation record to the medication recipient, as described above.

Figure 13:
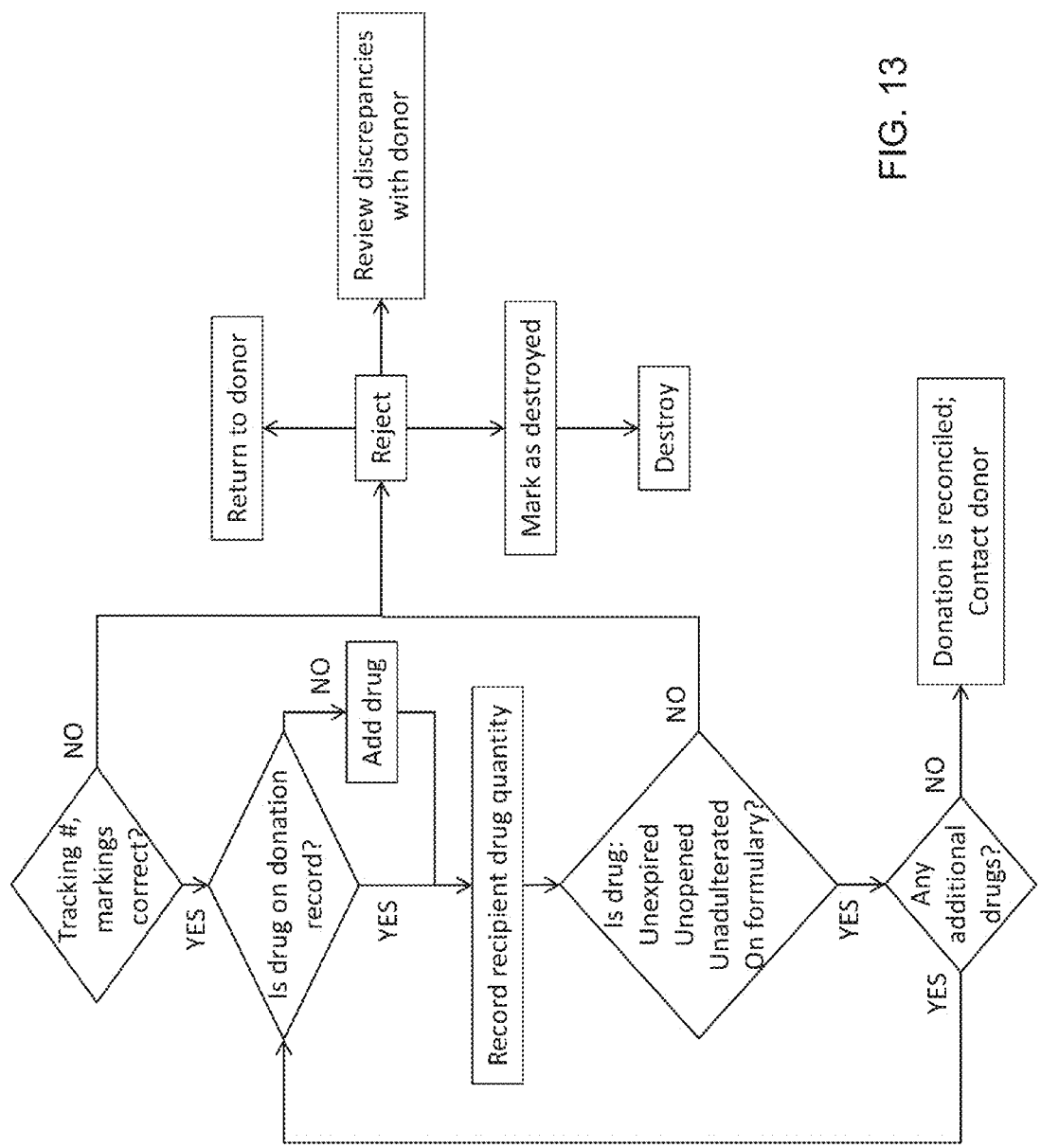
FIG. 13 is a flow chart illustrating a method for reconciling a medication donation, in accordance with some implementations.

FIG. 13 illustrates methods for reconciling a received medication donation, according to some implementations. These methods may be used by a medication recipient who receives a donation with or without a facilitator. As shown in FIG. 8 and FIG. 13, the medication recipient may first verify that the shipment tracking number, shipping label, shipping container, and/or any other distinctive markings are as expected. If these are correct, the medication recipient may, in some implementations, check the donation inventory against the donation record. On a medication-by-medication basis, the medication recipient may record the medication quantity. Any medication listed on the donation record but not received may be removed, and any medication not listed on the donation record may be added (with its name and quantity). The medication recipient may then check the condition of each medication, e.g., by verifying that it is unexpired, not opened or otherwise tampered with, unadulterated, and on-formulary. This step ensures that each medication is suitable for dispensing to a patient.

As shown in FIG. 13, if the shipment does not appear as expected, or if any medication is unsuitable for patient use, the shipment and/or medication(s) may be rejected by the medication recipient. The medication recipient has several ways to deal with a rejected medication. In some implementations, the medication recipient may return a rejected medication to the medication donor. In some implementations, the medication recipient may mark the rejected medication as destroyed, and either destroy the medication or provide it to a facility or service that destroys the medication. In some implementations, the medication recipient may further review any discrepancies, for example an incorrect tracking number, shipping label or container, an expired or otherwise unsuitable medication, or a received medication not from the formulary, with the medication donor. Once each medication is reconciled against the donation record, the medication recipient may contact the medication donor and provide the reconciled donation record (e.g., by providing a recipient record).

Figure 14:
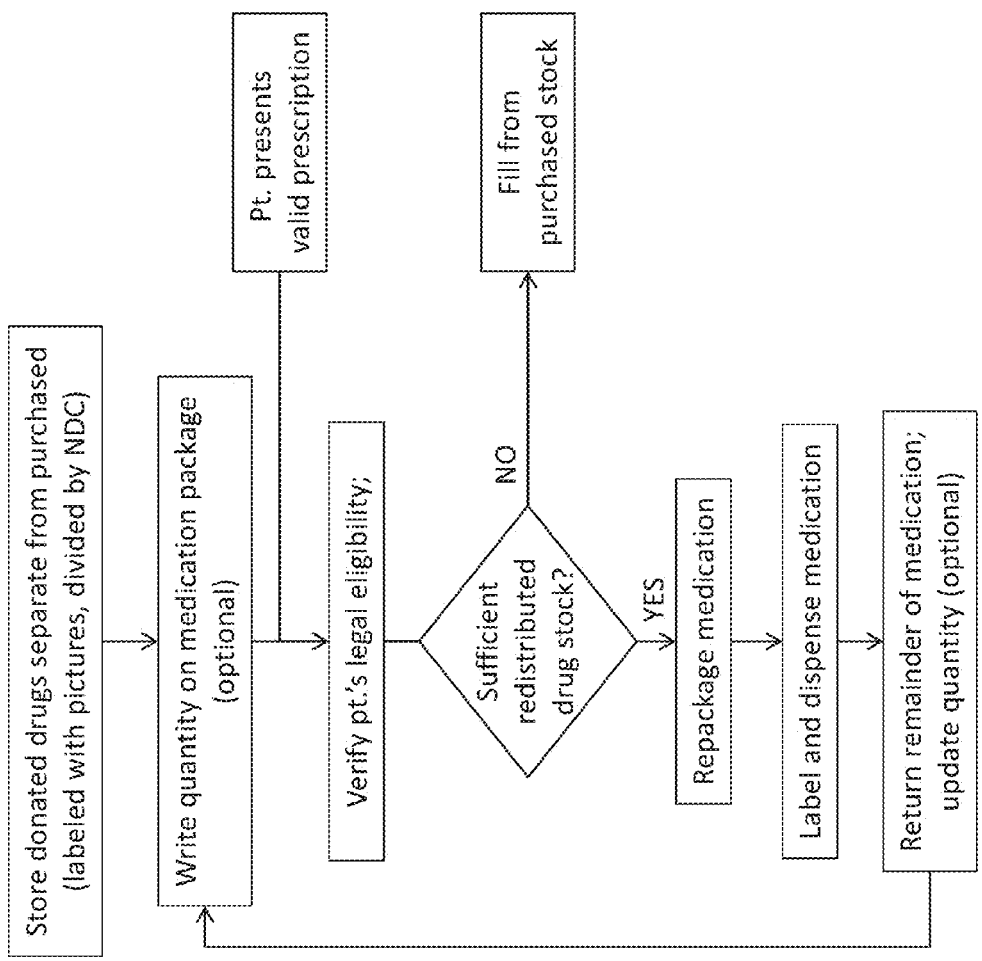
FIG. 14 is a flow chart illustrating a method for dispensing a donated medication, in accordance with some implementations.

FIG. 14 illustrates methods for dispensing a donated medication, according to some implementations. For legal, regulatory, and/or bookkeeping purposes, the medication recipient may choose to store donated medication(s) separately from purchased drug stock. As many donated medications may be packaged in the form of bubble or blister packs, donated medication(s) may be stored such that they are each labeled by name, strength, and optionally, a picture of the medication (for easy and reliable identification). Donated medication(s) may further be organized by National Drug Code, or NDC. Each pack may also be labeled with the medication quantity. Upon presentation of a valid patient prescription, the medication recipient may verify that the patient is eligible to receive the donated medication, e.g., by verifying that the patient is legally eligible to receive the donated mediation. In some implementations, a patient's legal eligibility to receive a donated medication may be determined, e.g., by consulting applicable federal or state laws, regulations, county ordinances, and/or the policies & procedures of the medication recipient. If the donated medication stock is insufficient to fill the prescription in its entirety, the remainder of the prescription may be filled using purchased drug stock. If the donated medication stock is sufficient, in some implementations, donated medication may be repackaged for filling the prescription, which may include de-blistering, placing the medication in a new bottle or other container, and removing or otherwise obfuscating existing patient information that may be present from the medication donor. In some implementations, the donated medication may then be properly labeled with the correct patient information and dispensed to the patient. In some implementations, the donated medicine may be repackaged. In some implementations, repackaging may include obfuscating and/or removing any patient information existing before the donation of the medicine, such that it is not visible or legible to the new patient to whom the donated medication is dispensed. After dispensing medication, any remaining donated medication may be returned to storage, and the quantity may be updated.

Certain aspects of the present disclosure relate to computer readable storage media for facilitating or receiving a medication donation. In some implementations, a computer readable storage medium may be configured to include instructions for receiving recipient and donor information, as described herein. As used herein, a suitable computer readable storage medium may include a non-transitory computer readable storage medium, such as high-speed random access memory and/or non-volatile memory (e.g., one or more magnetic disk storage devices, one or more flash memory devices, one or more optical storage devices, and/or other non-volatile solid-state memory devices).

In some implementations, the computer readable storage medium may be configured to include instructions for approving the medication donor as eligible to donate a medication from the formulary, the medication recipient as eligible to receive a medication from the formulary, or both, using a computer processor. The computer readable instructions stored on the computer readable storage medium may include one or more of: source code, assembly language code, object code, or other instruction format that is interpreted by the computer processor(s). In some implementations, the computer readable storage medium may be configured to include instructions for communicating the donor information to the recipient and/or communicating the recipient information to the donor. In some embodiments, at least one or both of the donor information and the recipient information may be communicated to the other party through an Internet-based platform using the computer readable storage medium described herein.

In some implementations, the donor information and the recipient information are received as electronic records and stored in a database. In some implementations, the electronic records and/or database may be stored on any suitable computer readable storage medium described herein, e.g., as part of a computer system with a processor and memory.

Certain aspects of the present disclosure relate to a computer-implemented system for facilitating or receiving a medication donation. In some implementations, the system may include a processor and memory. As used herein, a processor may include any processor known in the art suitable for a computer-implemented system described herein. As used herein, memory may include high-speed random access memory and/or non-volatile memory, or any other suitable memory known in the art. In some implementations, the memory may be configured to include computer readable instructions for receiving recipient and donor information, as described herein. In some implementations, the memory may be configured to include computer readable instructions for approving the medication donor as eligible to donate a medication from the formulary, the medication recipient as eligible to receive a medication from the formulary, or both, using a computer processor, as described above. In some implementations, the memory may be configured to include computer readable instructions for communicating the donor information to the recipient and/or communicating the recipient information to the donor.

FIG. 15 depicts computing system 1500 with a number of components that may be used to perform the above-described processes. The main system 1502 includes a motherboard 1504 having an I/O section 1506, one or more central processing units (CPU) 1508, and a memory section 1510, which may have a flash memory card 1512 related to it. The I/O section 1506 is connected to a display 1524, a keyboard 1514, a disk storage unit 1516, and a media drive unit 1518. The media drive unit 1518 can read/write a computer-readable medium 1520, which can contain programs 1522 and/or data.

At least some values based on the results of the above-described processes can be saved for subsequent use. Additionally, a computer-readable medium can be used to store (e.g., tangibly embody) one or more computer programs for performing any one of the above-described processes by means of a computer. The computer program may be written, for example, in a general-purpose programming language (e.g., Pascal, C, C++, Java) or some specialized application-specific language.

Although only certain exemplary embodiments have been described in detail above, those skilled in the art will readily appreciate that many modifications are possible in the exemplary embodiments without materially departing from the novel teachings and advantages of this disclosure. For example, aspects of embodiments disclosed above can be combined in other combinations to form additional embodiments. Accordingly, all such modifications are intended to be included within the scope of this technology.

The foregoing description, for purpose of explanation, has been described with reference to specific implementations. However, the illustrative discussions above are not intended to be exhaustive or to limit the disclosed implementations to the precise forms disclosed. Many modifications and variations are possible in view of the above teachings. The implementations were chosen and described in order to best explain the principles and practical applications of the disclosed ideas, to thereby enable others skilled in the art to best utilize them with various modifications as are suited to the particular use contemplated.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. A method of facilitating the donation of a pharmaceutical medication, comprising:
   (a) receiving recipient information from a medication recipient, wherein the recipient information comprises recipient registration information and a formulary, wherein the formulary comprises a list of one or more pharmaceutical medications sought to be received by the medication recipient, a list of one or more pharmaceutical medications not accepted by the medication recipient, or both, wherein the recipient registration information comprises name and address, and wherein the recipient registration information is stored as an electronic record on an electronic device comprising a processor and memory;
   (b) receiving donor information from a medication donor, wherein the donor information comprises donor registration information, wherein the donor registration information comprises name and address, and wherein the donor registration information is stored as an electronic record on the electronic device;
   (c) using the electronic device, connecting the medication donor to the medication recipient by at least one or both of providing the donor information to the recipient and providing the recipient information to the donor;
   (d) verifying that the medication donor has approved donating a pharmaceutical medication from the formulary to the medication recipient, and that the medication recipient has approved receiving a pharmaceutical medication from the formulary from the medication donor; and
   (e) transferring the pharmaceutical medication approved in (d) from the medication donor to the medication recipient, wherein the pharmaceutical medication is repackaged prior to dispensing the pharmaceutical medication to a patient, and wherein the repackaging includes one or more of: de-blistering the pharmaceutical medication, placing the pharmaceutical medication in a new bottle or other container, and removing or otherwise obfuscating existing patient information.

2. The method of claim 1, further comprising verifying the medication donor as eligible to donate a medication from the formulary based at least in part on donor license information, the medication recipient as eligible to receive a medication from the formulary based at least in part on recipient license information, or both.

3. The method of claim 1, wherein the medication recipient verifies the medication donor as eligible to donate a pharmaceutical medication from the formulary.

4. The method of claim 1, further comprising, after (d), receiving a donation record from the medication donor, wherein the donation record comprises a list of the name and quantity of each pharmaceutical medication to be sent by the medication donor to the medication recipient.

5. The method of claim 4, wherein the donation record is stored as an electronic record, and wherein the electronic record is stored on the electronic device.

6. The method of claim 4, further comprising providing the donation record to the medication recipient.

7. The method of claim 1, further comprising, after (d), receiving a recipient record from the medication recipient, wherein the recipient record comprises a list of the name and quantity of each pharmaceutical medication received by the medication recipient.

8. The method of claim 7, wherein the recipient record further comprises a status entry for each received pharmaceutical medication, and wherein the status entry indicates how the received medication was handled by the medication recipient.

9. The method of claim 7, further comprising providing the recipient record to the medication donor.

10. The method of claim 7, wherein the recipient record is stored as an electronic record, and wherein the electronic record is stored on the electronic device.

11. The method of claim 1, further comprising, after (d), providing a shipping label to the medication donor suitable for shipping the donation to the medication recipient.

12. The method of claim 1, further comprising, after (d), allowing the medication recipient to block the medication donor for a subsequent donation to the medication recipient.

13. The method of claim 1, further comprising, after (d), arranging a carrier pickup for a subsequent donation from the medication donor to the medication recipient.

14. The method of claim 1, further comprising, after (a), approving the one or more pharmaceutical medications from the formulary as eligible for donation.

15. The method of claim 1, further comprising, after (d), providing a shipping container to the medication donor suitable for shipping the donation to the medication recipient.

16. The method of claim 1, further comprising, after (d), providing a shipping manifest to the medication donor, wherein the shipping manifest comprises a list of one or more pharmaceutical medications in the donation and quantities of the one or more pharmaceutical medications in the donation.

17. The method of claim 1, wherein connecting the medication donor to the medication recipient comprises displaying a list of one or more medication donors to the recipient and receiving from the recipient a selection of a party for donating a pharmaceutical medication, displaying a list of one or more recipients to the donor and receiving from the donor a selection of a party for receiving a pharmaceutical medication, or both.

18. The method of claim 1, wherein the medication recipient is an entity eligible to receive and dispense a medication, or a third-party contracted to provide services on behalf of an entity eligible to receive and dispense a medication.

19. A method of receiving a donated pharmaceutical medication, comprising:
   (a) providing a formulary to a medication donor, wherein the formulary comprises a list of one or more pharmaceutical medications sought to be received from the medication donor, a list of one or more pharmaceutical medications not accepted from the medication donor, or both;
   (b) receiving registration information from the medication donor, wherein the registration information comprises name and address, and wherein the registration information is stored as an electronic record on an electronic device comprising a processor and memory;
   (c) approving the medication donor for donating the one or more pharmaceutical medications from the formulary based at least in part on donor license information, wherein the approval is stored as an electronic record on the electronic device;
   (d) receiving at least a portion of the one or more pharmaceutical medications from the formulary from the medication donor; and
   (e) dispensing the donated pharmaceutical medication, wherein dispensing the donated pharmaceutical medication comprises:
      (i) receiving a valid prescription for the donated pharmaceutical medication from a patient;
      (ii) verifying the eligibility of the patient to receive the donated pharmaceutical medication;
      (iii) repackaging the donated pharmaceutical medication;
      (iv) labeling the donated pharmaceutical medication; and
      (v) dispensing the labeled, donated pharmaceutical medication to the patient.

20. The method of claim 19, further comprising, after (d), receiving a donation record from the medication donor, wherein the donation record comprises a list of the name and quantity of each pharmaceutical medication sent by the medication donor.

21. The method of claim 20, wherein the donation record is stored as an electronic record on the electronic device.

22. The method of claim 19, further comprising, after (d), creating a recipient record, wherein the recipient record comprises a list of the name and quantity of each pharmaceutical medication received.

23. The method of claim 22, wherein the recipient record further comprises a status entry for each received pharmaceutical medication, and wherein the status entry indicates how the received medication was handled.

24. The method of claim 22, further comprising providing the recipient record to the medication donor.

25. The method of claim 22, wherein the recipient record is stored as an electronic record on the electronic device.

26. The method of claim 19, further comprising, after (c), providing a shipping label to the medication donor suitable for shipping the donation to the medication recipient.

27. The method of claim 19, further comprising the step of arranging a carrier pickup for a subsequent donation from the medication donor.

28. The method of claim 19, further comprising providing the donation record to the medication recipient.

29. The method of claim 19, wherein (d) further comprises receiving one or more pharmaceutical medications that are not listed in the formulary or unsuitable for patient use, and wherein the method further comprises, after (d), rejecting the one or more pharmaceutical medications that are not listed in the formulary or unsuitable for patient use, and destroying or returning the rejected one or more pharmaceutical medications.

30. The method of claim 19, wherein repackaging the donated pharmaceutical medication comprises one or more of: de-blistering the donated pharmaceutical medication, placing the donated pharmaceutical medication in a new bottle or other container, and removing or otherwise obfuscating existing patient information.

31. The method of claim 19, wherein at least part of (d) or (e) is performed by a medication recipient; and wherein the medication recipient is an entity eligible to receive and dispense a medication, or a third-party contracted to provide services on behalf of an entity eligible to receive and dispense a medication.

* * * * *